Feb. 28, 1939. A. BURKWOOD Plant Pat. 315
DAPHNE
Filed June 11, 1938
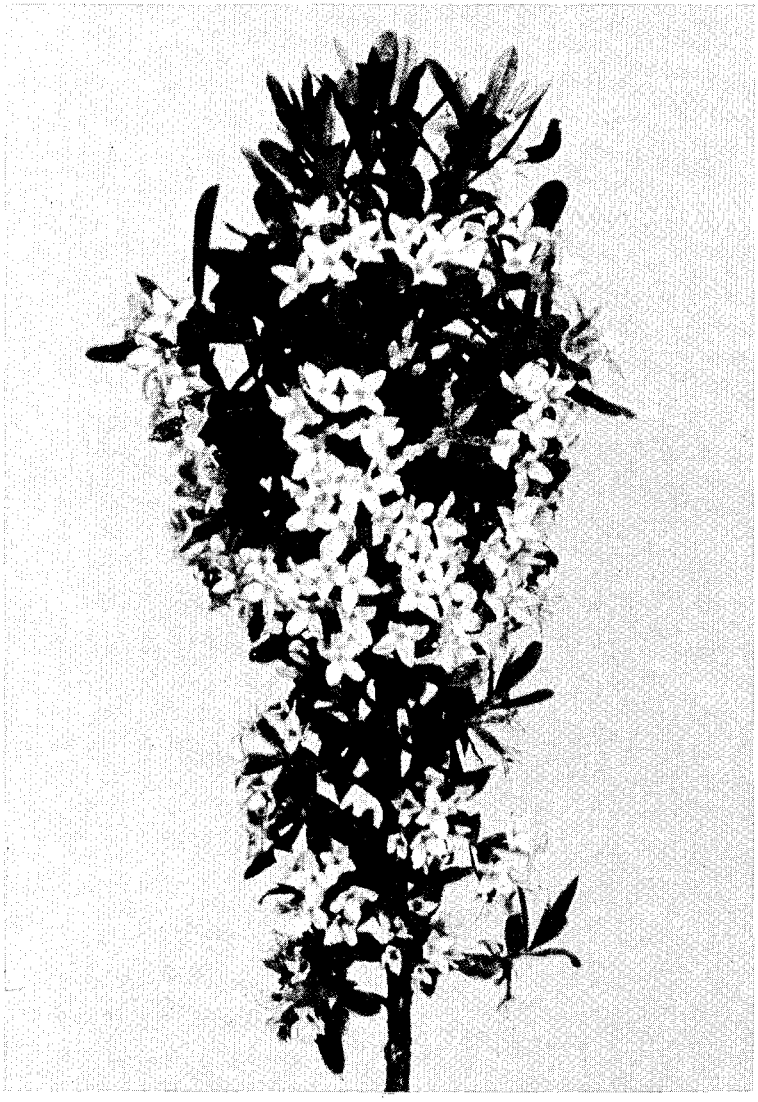
INVENTOR
ARTHUR BURKWOOD
BY John H. Leonard,
HIS ATTORNEY Patented Feb. 28, 1939

Plant Pat. 315

UNITED STATES PATENT OFFICE

315

DAPHNE

Arthur Burkwood, Farnham, England, assignor, by mesne assignments, to The Wayside Gardens Company, Mentor, Ohio, a corporation of Ohio Application June 11, 1938, Serial No. 213,198

1 Claim. (Cl. 47—60)

This invention relates to a new variety of a daphne flower and plant and to a method of producing the same. This new daphne plant was originated from a selected seedling produced by crossing *Daphne caucasica,* as the female parent, with *Daphne cneorum,* as the male parent. Since the first production of the new variety, large numbers of plants have been and are being reproduced asexually.

The plant of this new variety is an exquisite shrub possessing great decorative value in its distinctive bushy habit of growth, in its sturdy character and appearance, and in its formation of a neatly rounded sub-evergreen bush reaching a maximum height of about three feet. The good nature of the plant's rooting system permits transplanting of the shrub without difficulty at any time during the dormant season, and it facilitates materially in the successful cultivation of the plant.

This attractive hybrid, which is characteristically a vigorous grower, bears foliage of broadly lanceolate leaves abundantly produced and of a pale or greyish green colour, corresponding to Maerz and Paul, Plate No. 23L–5. The common peduncle or stalk presents a very rugged appearance and it ably supports the abundance of flowers and leaves growing on peduncles or terminal branches issuing therefrom.

Flowers appear on the shrub at any time during the growing season, although the principal flowering period is in the spring, during which time flowers are profusely produced. During the autumn season flowers are present on the shrub in the later stages of development. The individual, long-tubed, fragrant flowers are borne in profusion in a terminal cluster and less densely on the terminal branches issuing from a common peduncle, and they are distinctively larger in size than those of the parents and unusually large in size for a daphne, measuring as much as three-quarters of an inch in diameter. The flowers possess a strong and inviting fragrance and they are of a characteristically pale pink colour, Plate No. 1A–2, whilst the reverse sides of the petals are of a deeper pink or red colour, Plate No. 1K–12, which greatly magnify the delicacy of the flower coloring.

Generally, this new plant is a distinctive improvement over the present known daphne varieties.

The drawing shows my daphne in its natural colours as near as it is possible to produce artificially, and it illustrates other distinctive characteristics which distinguish my new daphne variety over the parent stock and other known varieties of daphne.

Having now fully shown and described my new daphne and the method of producing and reproducing the same, what I claim and desire to secure by Letters Patent of the United States is:

A daphne as herein shown and characterised by its vigorous sturdy and bushy habit of growth in forming a neatly rounded sub-evergreen bush, its rooting system, its prolific foliage of a pale or greyish green colour, its profuse flowering habit in the spring, and its continual flowering habit throughout the growing season, its flower size and growth, and its long-tubed, very fragrant flowers of a pale pink colour with deeper colored buds borne in profusion in a terminal cluster and less densely on terminal branches issuing from a common peduncle.

ARTHUR BURKWOOD.